United States Patent
Wijbrans et al.

(10) Patent No.: US 10,018,559 B2
(45) Date of Patent: Jul. 10, 2018

(54) TISSUE INSPECTION SYSTEM WITH OPTICAL FIBERS AND CONTINUOUS CALIBRATION

(71) Applicant: KONINKLIJKE PHILIPS N.V., Eindhoven (NL)

(72) Inventors: Klaas Cornelis Jan Wijbrans, Eindhoven (NL); Gerhardus Wilhelmus Lucassen, Eindhoven (NL); Bernardus Hendrikus Wilhelmus Hendriks, Eindhoven (NL); Christoph Dobrusskin, Eindhoven (NL); Cornelis Reinder Ronda, Eindhoven (NL); Johannes Joseph Hubertina Barbara Schleipen, Eindhoven (NL); Johannes Antonius Rooij, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/567,305

(22) PCT Filed: Apr. 13, 2016

(86) PCT No.: PCT/EP2016/058144
§ 371 (c)(1),
(2) Date: Oct. 17, 2017

(87) PCT Pub. No.: WO2016/166176
PCT Pub. Date: Oct. 20, 2016

(65) Prior Publication Data
US 2018/0088044 A1 Mar. 29, 2018

(30) Foreign Application Priority Data
Apr. 17, 2015 (EP) .................................. 15163957

(51) Int. Cl.
*G01J 3/44* (2006.01)
*G01N 21/47* (2006.01)
(Continued)

(52) U.S. Cl.
CPC ............. *G01N 21/474* (2013.01); *A61B 1/07* (2013.01); *A61B 5/0075* (2013.01);
(Continued)

(58) Field of Classification Search
CPC .. G01N 21/474; G01N 21/4785; G01N 21/47; G01N 21/65; G01N 2021/658; A61B 1/07; A61B 5/0084; G01J 3/02; G01J 3/44
See application file for complete search history.

(56) References Cited

U.S. PATENT DOCUMENTS

| 4,459,044 | A | 7/1984 | Alves |
| 4,900,933 | A | 2/1990 | Nestor |

(Continued)

FOREIGN PATENT DOCUMENTS

| EP | 0283289 A2 | 9/1988 |
| JP | 3287050 A | 12/1991 |

(Continued)

OTHER PUBLICATIONS

Mignani, Anna Grazia et al "Biomedical Sensors using Optical Fibres", Rep. Prog. Phys. vol. 59, 1996, pp. 1-28.
(Continued)

*Primary Examiner* — Abdullahi Nur (57) ABSTRACT

A system for tissue inspection is provided, comprising a console (50) with a light source (64), a spectrometer (66), an optical switch (65) and a processing unit. The system further comprises an elongated shaft (10), wherein an illumination fiber (40), a plug (50) in front of the illumination fiber (40), and a detection fiber (41) is provided in the elongated shaft
(Continued)

(10). The illumination fiber (40) is capable of transmitting light from the light source (64) to its front surface and is capable of transmitting light being back-reflected from the plug (50) to the optical switch (65). The detection fiber (41) is capable of transmitting light reflected from tissue in front of the distal end surface of the elongated shaft (10) to the optical switch (65). The optical switch (65) is configured to provide the back-reflected light to the spectrometer (66) for generating a reference spectrum and to provide the light reflected from the tissue to the spectrometer (66) for generating a diffuse reflectance spectrum. The processing unit is configured to generate a tissue spectrum by normalizing the diffuse reflectance spectrum with the reference spectrum.

13 Claims, 5 Drawing Sheets

(51) Int. Cl.
*A61B 5/00* (2006.01)
*A61B 1/07* (2006.01)
(52) U.S. Cl.
CPC ....... *A61B 5/0084* (2013.01); *G01N 21/4785* (2013.01); *A61B 2560/0223* (2013.01); *G01N 2021/4742* (2013.01)

(56) References Cited

U.S. PATENT DOCUMENTS

| | | |
|---|---|---|
| 6,167,297 A | 12/2000 | Benaron |
| 6,399,397 B1 | 6/2002 | Zarling |
| 6,711,426 B2 | 3/2004 | Benaron |
| 7,241,287 B2 | 7/2007 | Shehada |
| 7,813,778 B2 | 10/2010 | Benaron |
| 2007/0093703 A1* | 4/2007 | Sievert, Jr. ........... A61B 5/0084 600/343 |
| 2010/0111136 A1 | 5/2010 | Huang |
| 2013/0100439 A1 | 4/2013 | Yu |
| 2014/0192362 A1 | 7/2014 | Takaoka |

FOREIGN PATENT DOCUMENTS

| | | |
|---|---|---|
| WO | 2014162289 A1 | 10/2014 |
| WO | 2015121147 A1 | 8/2015 |

OTHER PUBLICATIONS

Kozaki, Tokuya et al "Recent Progree of High-Power GaN-based Laser Diodes", Proc. of SPIE vol. 6485 648503-1, 2007.

Farrell, T.J. et al "A diffusion theory model of spatially resolved, steady-state diffuse reflectance for the non-invasive determination of tissue optical properties," Med. Phys. 19 (1992) p. 879-888. Abstract Only.

Nachabe, Rami et al "Estimation of lipid and water concentrations in scattering media with diffuse optical spectroscopy from 900 to 1600 nm", J. Biomed. Opt. 15, 037015 (2010).

* cited by examiner

TISSUE INSPECTION SYSTEM WITH OPTICAL FIBERS AND CONTINUOUS CALIBRATION

CROSS-REFERENCE TO PRIOR APPLICATIONS

This application is the U.S. National Phase application under 35 U.S.C. § 371 of International Application No. PCT/EP2016/058144, filed on Apr. 13, 2016, which claims the benefit of European Patent Application No. 15163957.2, filed on Apr. 17, 2015. These applications are hereby incorporated by reference herein.

FIELD OF THE INVENTION

The invention generally relates to a system including optical fibers. Particularly, the invention relates to a system including an interventional device with optical fibers, wherein the system provides continuous calibration of the light path through the fibers.

BACKGROUND OF THE INVENTION

In order to position for example a needle under image guidance more accurately in a suspicious tissue, tissue sensing at the tip of the device may be of interest. Current needles often do not have such tissue feedback possibilities. Recently, elongated interventional devices have been reported with optical fibers integrated into the device which provide feedback from the tissue at the tip of the device. Such devices allow for fine-guidance towards small volumes of suspicious tissue, in particular for tissue which does not show sufficient contrast in imaging. In order to allow tissue discrimination, these devices employ diffuse reflectance spectroscopy (DRS).

A so called photonic needle allows for determining tissue type by sending light with a broadband spectrum into the body through one or more illumination fibers and measuring the reflected spectrum and determining the type of tissue by the application of an algorithm on this spectrum through one or more collection fibers. This is a diffuse reflectance measurement that may be obtained by normalizing the measured tissue spectrum with a previously measured reference spectrum. This requires either frequent calibration with a reference spectrum which is cumbersome in the workflow in a hospital, or piece-wise calibration together with a very tight control over the stability of all components in the optical path resulting in high cost and a constraint to large core fibers making the use of smaller needles than G21 not feasible.

SUMMARY OF THE INVENTION

It can be seen as an object to provide a system including optical fibers, wherein the system provides continuous calibration of the light path. This and other objects are solved by the system according to the independent claim. Further embodiments are described in the dependent claims.

In general, a system for tissue inspection in accordance with the invention, comprises a light source, a light detector and/or spectrometer, an optical switch and a processing unit. All these element may be provided in a console, but for example the processing unit may also be located outside of the console, e.g., included in what is drawn as the display for instance a tablet, so as to control the remainder of elements. Otherwise, the element may also be provided in separate units.

The system further comprises an elongated shaft including a distal end surface wherein an illumination fiber, a plug in front of the illumination fiber, and a detection fiber is provided in the elongated shaft. The illumination fiber may be made of a first material having a first refractive index, wherein the plug is made of a second material having a second refractive index, wherein the second refractive index differs from the first refractive index so as to allow back-reflectance of light.

The illumination fiber as well as the detection fiber may be arranged in a channel extending through the elongated shaft and forming open ends in the distal end surface, so that the front surface of the illumination fiber may be located inside a first channel and adjacent to the distal end surface of the elongated shaft and the detection fiber may be arranged in a second channel of the elongated shaft so that the front surface may be located in the plane defined by the distal end surface. Otherwise, the elongated shaft may be hollow and the two fibers may for example be glued to opposite walls leaving a single large open channel.

The plug may be arranged in front of the illumination fiber so that the first surface of the plug is optically connected with the illumination fiber and the second surface lies in a plane defined by the distal end surface of the elongated shaft.

Optionally, the illumination fiber is arranged in the elongated shaft so that a front surface of the illumination fiber is located inside the elongated shaft, and the front surface of the illumination fiber is adjacent to the first surface of the plug.

The illumination fiber is capable of transmitting light from the light source to its front surface and is capable of transmitting light in an opposite direction, i.e. being for example back-reflected from the plug to the optical switch. The detection fiber is capable of transmitting light reflected from tissue in front of the distal end surface of the elongated shaft to the optical switch. The optical switch is configured to provide the back-reflected light to the spectrometer for generating a reference spectrum and to provide the light reflected from the tissue to the spectrometer for generating a diffuse reflectance spectrum. The processing unit is configured to generate a tissue spectrum by normalizing the diffuse reflectance spectrum with the reference spectrum.

A main aspect of such a system is the provision of a continuous reference spectrum. Therefore, the workflow in the hospital may be improved by removing any warm-up period and reference spectrum calibration. Instead, the system may be instantaneously available at the moment of switching on. Further, the system removes the need for spectral stability of all individual optical components including the optical fiber, at least when the same type of fiber is used for both detection fiber and illumination fiber and the fibers are routed together to exhibit the same bending for the duration of the procedure. According to this aspect the reference spectrum originates at the first surface of the plug, i.e. at the distal end of the illumination fiber. The light reflected from the tissue, which is collected by the detection fiber for generating the diffuse reflectance spectrum, likewise originates at the distal end of the detection fiber. When the illumination fiber and detection fiber are routed together as described above, i.e. they share a common path, the impact of physical conditions on the optical fibers, such as changes in temperature and fiber bending, affect the optical fibers in the same way. Thus when the tissue spectrum is generated by normalizing the diffuse reflectance spectrum with the reference spectrum, common mode effects are cancelled resulting in an improved calibration.

As a result, the system is then also usable for extended periods of time and insensitive to environmental variations. Consequently, costs of optical components decreases significantly due to the relaxed requirements on optical stability and the ability to deal with large variations, costs of manufacturing decreases because large tolerances are allowed for the total chain. On the other hand, the system enables the use of a higher intensity illumination light source, with the result of (i) lower cost of optical path because high volume standard telecom fibers and standard telecom connectors can be used, (ii) smaller size needles due to the use of high volume standard telecom fibers (125 um diameter) versus the current large core fibers (250 um diameter), (iii) lower cost due to the use of standard NA fibers (0.22) versus specialty high NA fibers (0.28).

According to an embodiment, an element may be provided between the front surface of the illumination fiber and the plug, wherein the element is made of a third material comprising phosphor. The illumination fiber may further be capable of transmitting phosphorescence light and the optical switch may further be capable of providing the phosphorescence light to the spectrometer for generating a reference spectrum. By selecting a phosphor mix that also contains line emitters, not only reference spectrum calibration but also wavelength shift of the spectrometers may be compensated continuously.

According to an embodiment, the light source of the system may comprise an LED or laser light source for exciting the phosphor of the element between the illumination fiber and the plug. The LED or laser light source may, for example, be blue; although other colors, or emission wavelengths, for example corresponding to infrared or ultraviolet wavelengths are also suitable. Furthermore, the light source may be adapted to emit light pulses. The system enables the use of very high pulsed light output when a LED or laser is used as excitation source for a phosphoric element in the light path. Therefore, the system is no longer influenced by the intensity of the environmental light. Latency is decreased significantly due to the much shorter measurement period, enabling real-time feedback to the end user. Movement of the disposable in the tissue during the measurement is no longer an issue because it can only move for a very short distance during the measurement period, resulting in reliable tissue measurements.

By modifying the optical path to also measure the back reflection at least of the remote phosphor into the illumination fiber, a continuous reference spectrum may be obtained for the total optical path. Thus, the need for tight control of the optical qualities of the disposable can be removed resulting in reduced cost. Any modifications in the spectral response of this back-reflected light due to absorption in the optical fiber itself, can be compensated for explicitly by e.g. using a set of calibration data belonging to this respective optical fiber and obtained during manufacturing of the optical fiber, or compensated for implicitly by using the same type of optical fiber for the illumination and detection fiber.

By using an element with phosphor adjacent the tip, a much higher light output can be achieved with much lower input power, thus (i) enabling a reduction of the fiber size, (ii) a reduction of the total power consumption, (iii) enabling smaller size needles at a lower cost through the re-use of standard telecom fibers. Further, biosafety is improved because the light source can be pulsed and only emits in the relevant wavelengths. Especially, any wavelengths below the excitation light source (e.g., UV) are completely absent. By carefully selecting the phosphor mix, the SNR of the total system can be optimized for the bands of interest in the spectrum. It is noted that 'adjacent' means within a few millimeters, i.e. less than the diameter of the shaft, in other words less than 1 mm up to 5 mm.

According to an aspect of the invention, a method is provided. The method comprises:
a) emitting light from a light source
b) coupling the light from the light source into an illumination fiber;
c) transmitting the light through the illumination fiber;
d) transmitting light back through the illumination fiber to the an optical switch;
e) reflecting spectrally modified light from tissue into a detection fiber;
f) transmitting the collected spectrally modified light to the optical switch,
g) providing both light from the illumination fiber and light from the detection fiber to a spectrometer using the optical switch;
h) normalizing the light from the detection fiber based on the light received from the illumination fiber using the spectrometer.

According to an embodiment of the method, in step d), the transmission of light back through the illumination fiber is achieved (i) as a back-reflection from a front surface of the illumination fiber, or (ii) from an excited phosphor located adjacent the distal end surface.

Summarized, the system may comprise:

A console being capable of sending and receiving light via at least a pair of fibers.

The console may use a led or laser light source to create a high brightness illumination.

The console may pulse the led or laser to allow frequent background measurements and thereby lower the average power on the tissue.

The console may contain a dichroic splitter and shutter or multiplexer as an optical switch to enable spectral measurement of the returned light in the illumination fiber.

The pair of fibers may be bundled together in a plastic protective tube or cable.

The elongated device may contain an element including phosphor between the tip of the illumination fiber and the distal end surface of the elongated device, which is capable of transforming the illumination light, which may for example be blue illumination light to a broadband spectrum through phosphorescence.

The phosphorescence light may be sent directly into the tissue via the distal end surface as well as directly returned into the illumination fiber which serves as the continuous reference spectrum. Because of the high attenuation of backscattering, the effect of tissue on the returned signal in the illumination fiber may be less than $10^{-4}$.

The backscattered phosphorescence light via the tissue may be accepted in the distal end surface of a detection fiber.

The detection fiber may guide the light towards a spectrometer in the console.

The spectrometer may measure both the continuous reference spectrum signal and the diffuse reflected tissue signal.

The tissue spectrum may be calculated by normalizing the diffuse reflected tissue signal with the reference signal.

In accordance with an embodiment, the elongated shaft may further comprise a bevel so that the distal end surface may be arranged with an acute angle to a longitudinal axis of the elongated shaft. It is noted that also a blunt or pointed end or a part-spherical end of an elongated shaft may be adapted to be introduced into tissue.

In the following, geometrical aspects will be defined for a better understanding. First of all, the device includes a longitudinal main axis, usually the center axis of a rotationally symmetrical shaft. Further, the tip portion of the device may be cut at an angle to the main axis forming the bevel. The pointed tip of the bevel may be directed to the 'front' of the needle. As a result, looking from the 'side', i.e. 'laterally', it is possible to recognize the angle between the bevel and the main axis.

A 'bevel' is a geometrical structure for introducing a device, for example a needle into tissue. Usually, a shaft of the device includes a circular cross section. The distal end of the shaft is cut such that an oval surface may be formed, which may be considered as being inclined relative to the longitudinal axis of the shaft. The bevel forms a pointed tip at the most distal end of the biopsy device. It should be noted that the bevel might form an acute angle with the shaft, such that the device includes a pointed tip. The acute angle might be between 20° and 40°.

It should be noted that the end surface of an optical fiber at an opening in the bevel may have a circular shape or a more or less oval shape in case of a substantially circular cross section of the fiber. Depending on the angle at which the fiber ends at the bevel surface, the shape of the end surface of the fiber will be effected and therefore also the direction of the emitted or received light.

Due to the slanted bevel surface, the distance between the fiber ends may be greater than the diameter of the shaft. For example, the distance may be more than 1.1 times greater than the diameter. Particularly, the distance may be more than 1.25 times greater than the diameter. Preferably, the distance may be more than 1.5 times greater than the diameter. In other words, the distance between the fiber ends should be as large as possible. Such distances are measured from the central axis of one of the fibers to the central axis of the other one of the fibers.

According to an embodiment, the elongated shaft of the system comprises a plug with a first surface and a second surface, wherein the plug is arranged in the channel so that the first surface of the plug is in contact with the front surface of the illumination fiber for transmitting light from the illumination fiber through the plug, and the second surface lies in the plane defined by the bevel surface thus forming a smooth distal surface at the distal end of the device. The illumination fiber may be made of a first material having a first refractive index and the plug may be made of a second material having a second refractive index, wherein the second refractive index differs from the first refractive index. For example, the material of the plug may have a refractive index similar to that of water.

The second surface of the plug may have the size and shape of the opening formed in the bevel surface, so that a smooth distal surface without any gaps is formed at the distal end by the bevel surface and the second surface when the optical fiber together with the plug are accommodated within the channel.

At least one of the second surface of the plug and the front surface of the detection fiber may have a predetermined roughness for further improving the light path.

According to an embodiment may the front surface of the illumination fiber be straight cut, i.e. be arranged with an angle relative to the longitudinal axis of 90°. Otherwise, the angle may be in the range of 60° to 90°, or in the range of 60° to 80°. The angle between the front surface of the illumination fiber and the longitudinal axis influences the internal reflection of light and may be chosen depending on the intended relation of back-reflected light and light passing through the plug.

According to an embodiment, at least the second material may be adapted for a wide-band optical transmission and low attenuation.

According to a further embodiment, a reflective coating may be provided at a channel wall of the channels. It is noted that the coating may be provided in all channels, but also in only one or two of the channels. Furthermore, it may be advantageous to provide the coating only in a section of a channel.

According to an embodiment, the system may further comprise an interconnecting cable with optical fibers for interconnecting the illumination fiber and the detection fiber with the console including an optical switch.

According to yet another embodiment, the elongated shaft may further comprise a tracking modality for tracking the elongated shaft within a tissue. A tracking modality for tracking the elongated shaft during fluoroscopy may be a radiopaque marker which is preferably arranged at or near the distal end of the elongated shaft. A tracking modality for tracking the elongated shaft in a magnetic field of a magnet tomography system may be a passive LC circuit, preferably arranged at or near the distal end of the elongated shaft. The tracking modality may, for example be used to determine the position and/or the orientation of the elongated shaft.

The system may further comprise a display device for displaying results of the tissue inspection, wherein the tissue inspection may be performed based on at least one of diffuse reflectance spectroscopy, diffuse optical tomography, differential path length spectroscopy, and/or Raman spectroscopy.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematic only, and not to scale. It is noted that similar elements are provided with the same reference signs in different figures, if appropriate.

DETAILED DESCRIPTION OF EMBODIMENTS

Figure 1:
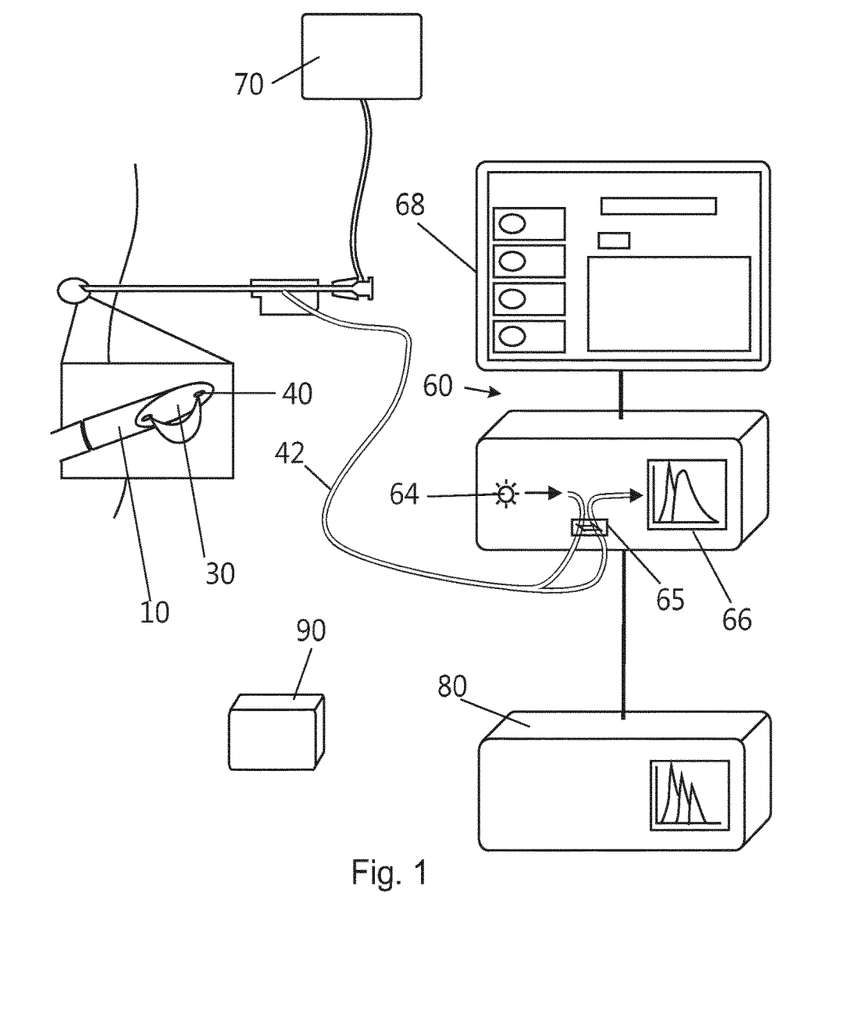
FIG. 1 shows a system in accordance with an embodiment.

FIG. 1 shows a system providing continuous calibration. As shown in the figure, the fibers 40 in the elongated shaft 10 are connected via an optical cable 42 to an optical console 60. The optical fibers can be understood as light guides or optical waveguides. In an embodiment, the console 60 comprises a light source 64, an optical switch 65, and an optical detector or spectrometer 66. The optical light source may be provided in form of a halogen broadband light source with an embedded shutter or in form of a laser or an LED. The optical detector 66 can resolve light with a wavelength substantially in the visible and infrared regions of the wavelength spectrum, such as from 400 nm to 1700 nm. The combination of light source 64 and detector 66 allows for diffuse reflectance measurements.

Figure 5:
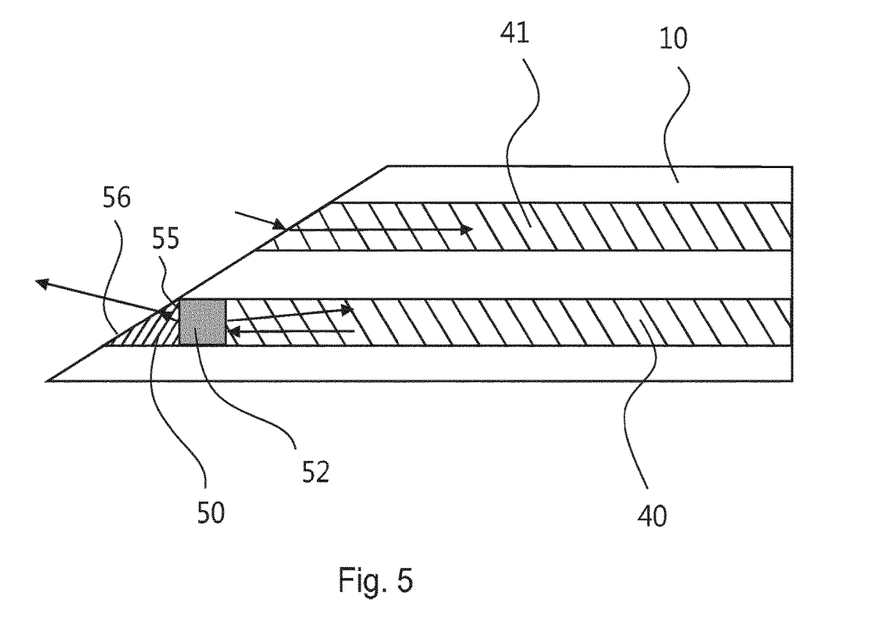
FIG. 5 illustrates a distal end portion of an elongated shaft according to a second embodiment.

In the elongated shaft, as shown in FIG. 5, an element 52 with phosphor may be provided, wherein the phosphor may be excited by the light source so as to emit phosphorescence, not only out of the distal end surface of the elongated shaft but also back through the illumination fiber to the console. The excited phosphor will emit light in all directions, part of the light is thus emitted via the bevel end face to tissue and back reflected phosphor light emission is directed towards the detectors via a dichroic mirror (transmitting laser light, reflecting broadband light) and a beam switch in the collection path, which alternatingly or on request guides either the light from the detection fiber or the back-reflected light from the illumination fiber to the detectors. This back reflected light is used as reference spectrum calibration of the total optical path, i.e., the spectral transfer function of the tissue is calculated by normalizing the measured spectrum from the detection fiber with the measured back-reflected spectrum from the illumination fiber.

A light source providing a better excitation of the phosphor may be a laser (e.g. a semiconductor laser), a light-emitting diode (LED) or a filtered light source, such as a filtered mercury lamp. For excitation of phosphor, a blue LED or a blue laser may be advantageous. The wavelengths emitted by the excitation light source may be shorter than the range of wavelengths of the detected light. It may be preferable to filter out the excitation light using a detection filter in order to avoid possible overload of the detector by the excitation light. A wavelength-selective detector, e.g. a spectrometer, is required when multiple phosphorescent/fluorescent entities are present that need to be distinguished from each other.

Optionally it is also possible that the console is coupled to an imaging modality capable of imaging the interior of the body, for instance when a biopsy is taken under image guidance. In this case it is also possible to store the image of the interior when the biopsy is taken to a container of the biopsy. In this case, in-vivo information of the optical biopsy needle, information of the pathology of the biopsy as well as the location where the biopsy was taken may be brought together for advanced pathology.

Further shown in FIG. 1 are a suction device 70, a device 80 for obtaining ex-vivo pathology information, and a storage container 90. The suction device may be connected to a proximal end of the elongated shaft, such that under-pressure or a vacuum can be applied through the elongated shaft, for example a biopsy device, to the distal end of the same.

The device 80 may be connected to the console 60 by means of a wire or wireless, for interchanging information like control commands or data representing pathological aspects of an inspected tissue sample. The device 80 may be a digital pathology systems consisting of an optical scanner and an image management system to enable digitizing, storage, retrieval, and processing of tissue staining images, reading the information stored in the storage box container, and integrating this information with the digitized staining data set, to be presented to the pathologist. In addition to this, the data set from the photonic biopsy device may be either presented next to the histopathology image or the two data sets may be fused in the image, characterized and recognizable by a certain coloring pattern of the image. For instance the oxygenation level measured in-vivo could be added as a red color, where deep red means low oxygenation and bright red would mean high oxygenation level. Additionally, molecular spatial distributions from FTIR or Raman could be added as a color coded mapping to the pathology slide of specific molecules.

The tissue sample, which may firstly be subjected to an in-vivo tissue inspection, i.e. an inspection within a living body, and which may secondly subjected to an ex-vivo tissue inspection by means of the device 80, may be situated in the container 90. Molecular diagnostics can also be performed on the tissue biopsy (e.g. sequencing or PCR), or part of the biopsy.

A processor transforms the measured spectrum into physiological parameters that are indicative for the tissue state and a monitor 68 may be used to visualize the results.

A computer program executable on the processor may be provided on a suitable medium such as an optical storage medium or a solid-state medium supplied together with or as part of the processor, but may also be distributed in other forms, such as via the Internet or other wired or wireless telecommunication systems.

Figure 2:
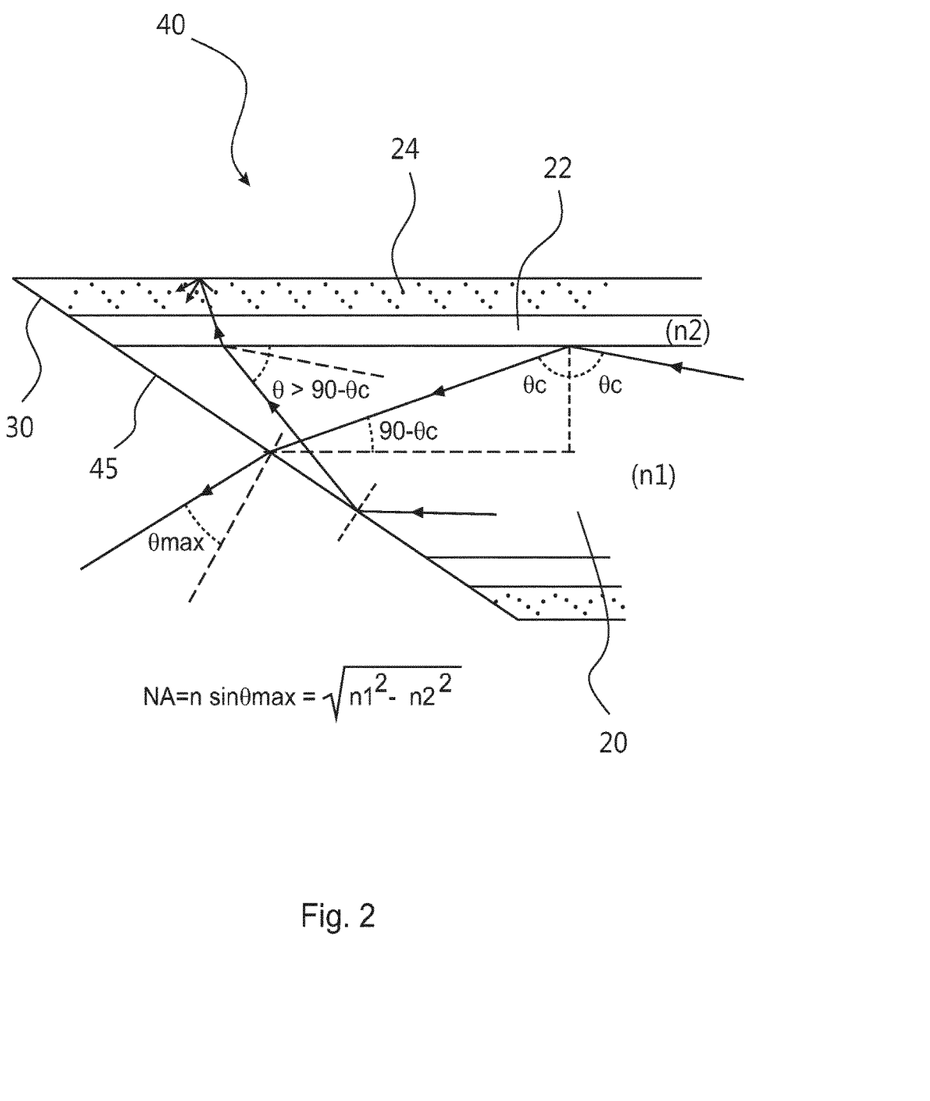
FIG. 2 shows an illustration of light reflection within an optical fiber.

FIG. 2 is a sectional view of a distal end portion of an optical fiber 40. The fiber includes a core 20, a cladding 22 and a buffer 24. As indicated by the arrows in FIG. 2, light is internally reflected for rays with an angle $\theta<90-\theta c$ where $\theta c$ is the critical angle at which the rays still undergo total internal reflection at the core cladding interface. Light coupling in or out from the fiber occurs for rays with angles $\theta<\theta max$. Internal reflection at a slanted fiber interface towards cladding and buffer causes reduced light output-coupling for illumination and in-coupling for detection since the angle $\theta$ for these rays will be $\theta>90-\theta c$ and do not undergo total reflection but is transmitted to the buffer and can be absorbed and scattered by the buffer material.

For example by applying a reflective coating to the sides of the lumen, the light hitting the sides of the lumen may be re-directed.

Figure 3:
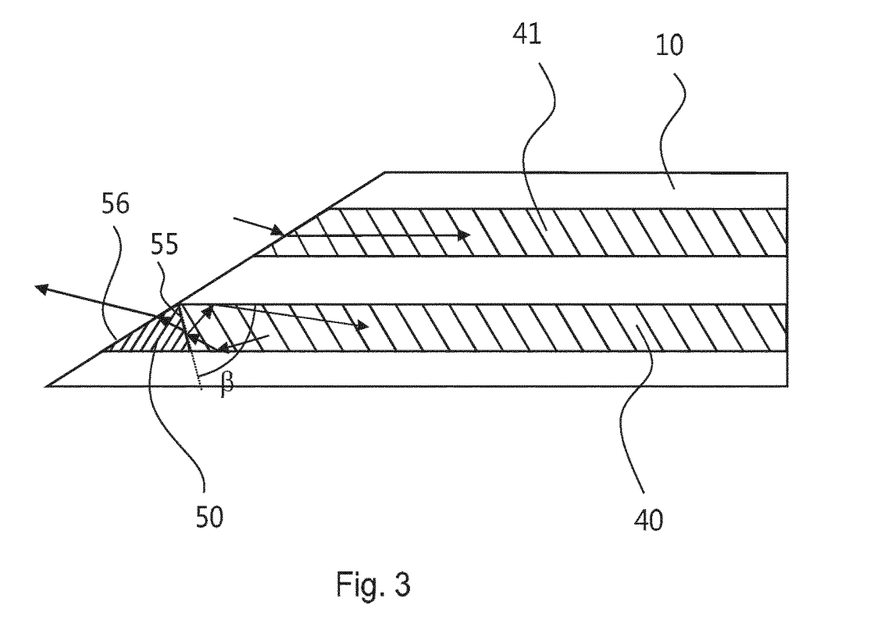
FIG. 3 illustrates a distal end portion of an elongated shaft according to a first embodiment.

In FIG. 3, a possibility for an improvement of the light output out of a fiber end is shown. In front of the optical fiber 40 a plug 50 may be provided, the plug having a first surface 55 being in contact with the front surface of the optical fiber, wherein the plug may be made from a plastic material with wide-band optical transmission and low attenuation like a Teflon based plastic, for example CYTOP that is used in Gigabit optical fibers. The plastic material of the plug is different to the material of the optical fiber 40, so that light refraction occurs at the contact surface. Exemplary beams of light are indicated in FIG. 3 by the arrow chains.

According to an embodiment, the contact surface between the optical fiber and the plug may be straight-cut being perpendicular to the longitudinal axis of the shaft. In the embodiment shown in FIG. 3, the first surface 55 between the fiber 40 and the plug 50 is slanted. This may additionally be used to direct the light in a specific direction. By adjusting the slanting angle $\beta$ of the fiber towards the plug, the direction of the beam can be steered upwards or downwards (or even sideways if that proves advantages). By using a different slant on the top and bottom fiber, the area where the cones of the two fibers cross can be adjusted. The angle and form of the contacting surfaces will influence also the amount of back-reflection of light.

The back-reflected light allows for a calibration. The back-reflection in the illumination fiber in the tip of the needle can further be achieved by a semi-transparent coating on the perpendicular fiber end face or the use of internal reflection on a slanted fiber edge. The amount of light back-reflected is tuned to give a good balance between light emitted into the tissue and the reference light, as well as the light collected from scattering in the tissue by the illumination fiber. A practical ratio could for example be 1% back-reflection, which is still a factor 100 higher than the collected light from the tissue so the reference measurement is not influenced by the tissue itself.

Instead of a refractive index difference, alternative embodiments can use a coating on the fiber end, a discrete layer with a higher or lower refractive index in between et cetera.

As a further improvement, plug 50 may have a cone shape. The cone shape allows for better emission of the light into the tissue. In addition, the exact position of the straight-cut fiber end becomes less critical and especially if a manufacturing process is used where first the fiber is inserted into the shaft 10 or an insert 35 and then the distal tip portions in form of plugs are molded into the resulting cavities. It is noted that the plug can compensate for tolerances in the exact end position of the fibers.

Figure 4:
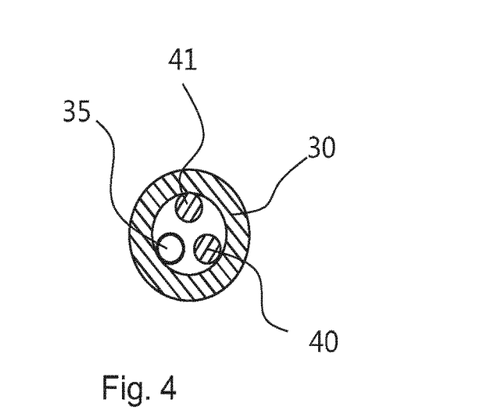
FIG. 4 is a front view of a device according to an embodiment.

In FIG. 4, an embodiment is shown, illustrating an arrangement of fibers 40 in a bevel surface 30 of a shaft 10, wherein the bevel surface 30 may be formed by a combination of a bevel surface of an insert and a co-planar bevel surface of an outer tubular shaft. It is noted that each of the fibers 40 may also be a combination of a fiber with a plug as described with respect to FIG. 3 or a combination of a fiber with a plug and a phosphoric element as described with respect to FIG. 5.

According to the embodiment of FIG. 4, the shaft comprises three channels each forming an opening in the bevel surface. In two of the channels, optical fibers 40 are accommodated, wherein the third channel 35 may be used as an injection or retraction channel. Such a channel may be an additional channel formed in the shaft or in an insert, and extending through that insert in a longitudinal direction, but may also be formed in the wall of the shaft or between the insert and the shaft or between the shaft and an additional outer tubular member. For example, the channel in which an insert is accommodated within the hollow shaft may be used for retracting a sample, after removing the insert, wherein a suction device may apply vacuum to the channel for retracting a sample of tissue. Alternatively, a retraction channel may be formed in the shaft or an insert between optical fibers which are preferably arranged as much as possible at opposite sides of the shaft or insert.

FIG. 5 shows the construction of the needle with optical fibers and an element 52 including phosphor in front of the illumination fiber. Like the plug, the phosphoric element may be only a few millimeters long when measured in a longitudinal direction of the illumination fiber, in particular smaller than the diameter of the shaft. The remote phosphor at the tip of the illumination fiber may be excited by laser or LED light. The end-face of the illumination fiber may be straight cut. In the embodiment of FIG. 5, the phosphor material is enclosed between the illumination fiber and a plug made of a low index material (e.g. transparent glue) to the bevel end-face. The detection fiber is polished flush with bevel angle.

It is noted that a simplified embodiment for continuous calibration can be implemented by only providing a feedback loop from the light source in the console to the spectrometers. In this case, the disposable illumination and detection fibers, and console fibers should have a fixed and known transfer function either by tight manufacturing tolerances, or pre-calibrated. Changes on to this transfer function by drift of the spectrometers and instability, warming-up and aging of the light source may be compensated for in a real-time feedback loop in the console.

Examples of devices with elongated shafts as described above may be single-use optical disposables and multi-use system connectors for fiber optical sensing applications (e.g., in the medical where sterility is of importance), for instance during needle interventions in the field of regional anesthesiology or during needle interventions in oncology, replaceable surgical knife and other optical tools during interventional procedures.

Figure 6:
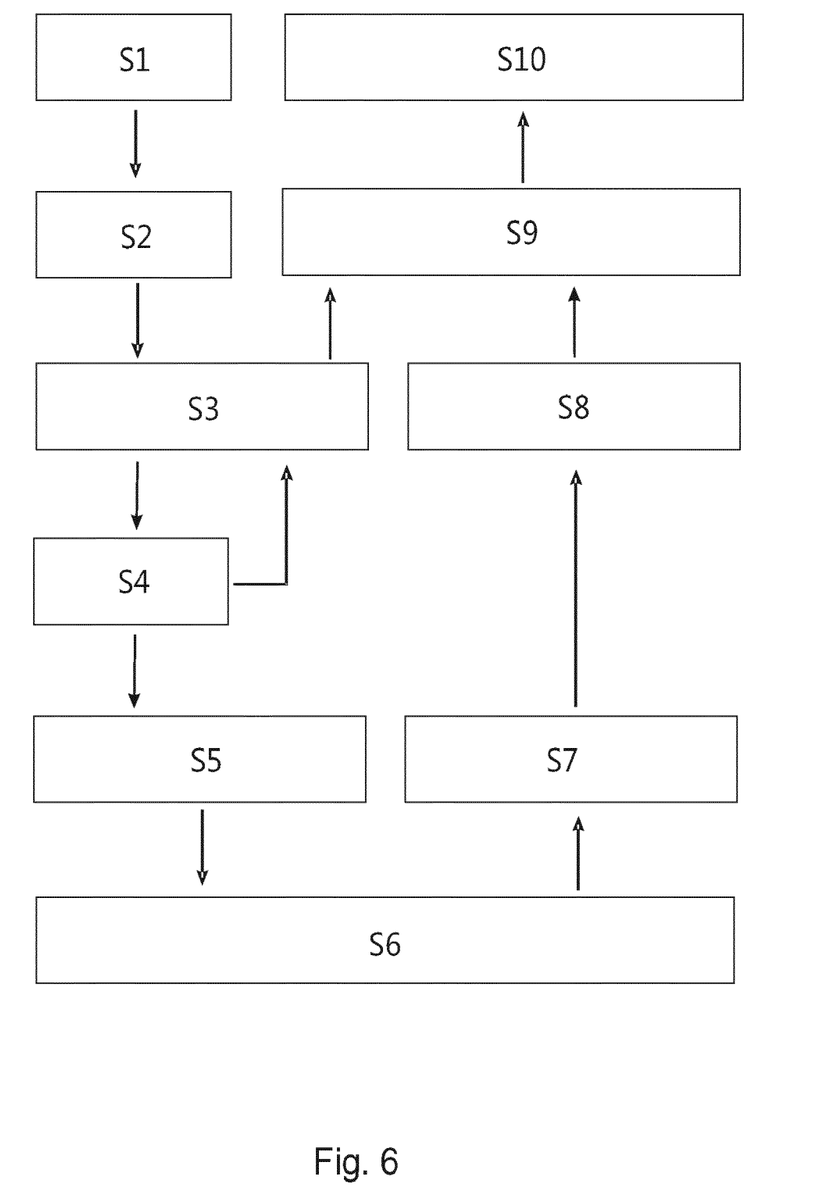
FIG. 6 is a flow chart illustrating steps of a method according to an embodiment.

The flow-chart in FIG. 6 illustrates principles performed in accordance with embodiments described herein. It will be understood that the steps described, are major steps, wherein these major steps might be differentiated or divided into several sub-steps. Furthermore, there might be also sub-steps between these major steps.

In step S1, a light source emits light. Either by filtering the light or as directly generated, light is coupled into an illumination fiber in step S2.

The light may be transmitted through the illumination fiber in step S3 and may be used to excite phosphor adjacent the distal end surface of an elongated shaft in step S4. Either from the excited phosphore of step S4 or as back-reflection at the front surface of the illumination fiber, light may be transmitted again through the illumination fiber (step S3) and to the optical switch in step S9.

The phosphor, excited in step S4, will emit phosphorescence light in step S5 towards the distal end surface of the elongated shaft, possibly through a plug in front of the element including phosphor. This light is emitted from the elongated shaft and into tissue in step S6.

From the tissue, spectrally modified light will be reflected back to the elongated shaft and into a detection fiber in step S7. The detection fiber transmits the collected light in step S8 to the optical switch, wherein the optical switch is configured to provide both light from the illumination fiber (step S3) and light from the detection fiber (step S8) to a spectrometer. The spectrometer may normalize in step S10 the light from the detection fiber based on the back-reflected light received from the illumination fiber.

According to an embodiment, a light source for generating light, for example blue light, illuminates a remote phosphor which emits broadband light that is used both to directly inform the spectrometer of the reference spectrum and illuminate the tissue so the spectrometer can determine the diffuse reflectance spectrum of the tissue as the ratio of the measured tissue spectrum and the measured reference spectrum.

The present invention is considered to extend to statements A-M:

A. A system for tissue inspection, comprising:
a light source (64), a spectrometer (66), an optical switch (65) and a processing unit,
an elongated shaft (10) including a distal end surface (30),
an illumination fiber (40) having a front surface (45), wherein the illumination fiber is made of a first material having a first refractive index and is arranged in the elongated shaft so that the front surface is located inside the elongated shaft, wherein the illumination fiber is configured to receive light from the light source,
a plug (50) with a first surface (55) and a second surface (56), wherein the plug is arranged in front of the illumination fiber so that the first surface of the plug is optically connected with the illumination fiber (40) and the second surface is located adjacent the distal end surface (30) of the elongated shaft, wherein the plug is made of a second material having a second refractive index, wherein the second refractive index differs from the first refractive index so as to allow back-reflectance of light in the illumination fiber, and a detection fiber (41) having a front surface, wherein the detection fiber is arranged in the elongated shaft so that the front surface is located adjacent the distal end surface (30), wherein the illumination fiber is capable of transmitting light from the light source (64) to its front surface and is capable of transmitting light from the plug to the optical switch (65), and wherein the detection fiber is capable of transmitting light reflected from tissue in front of the distal end surface to the optical switch, wherein the optical switch is configured to provide the light from the illumination fiber to the spectrometer for generating a reference spectrum and to provide the light from the detection fiber to the spectrometer for generating a diffuse reflectance spectrum, wherein the processing unit is configured to generate a tissue spectrum by normalizing the diffuse reflectance spectrum with the reference spectrum.

B. The system of statement A, wherein an element (52) made of a third material is provided between the front surface of the illumination fiber (40) and the plug (50), wherein the third material comprises phosphor, wherein the illumination fiber is further capable of transmitting phosphorescence light and wherein the optical switch is further capable of providing the phosphorescence light to the spectrometer for generating the reference spectrum.

C. The system of statement B, wherein the light source (64) comprises an LED or laser light source for exciting the phosphor of the element between the illumination fiber and the plug.

D. The system of any one of statements A to C, wherein the light source (64) is adapted to emit light pulses.

E. The system of any one of statements A to D, wherein the elongated shaft (10) further comprises a bevel (30) so that the distal end surface is arranged with an acute angle to a longitudinal axis of the elongated shaft.

F. The system of any one of statements A to E, wherein a reflective coating is provided at a channel wall of at least one of the channels.

G. The system of any one of statements A to F, wherein the at least one of the second surface of the plug (50) and the front surface of the detection fiber (41) has a predetermined roughness.

H. The system of any one of statements A to G, wherein the plug (50) has a length in a longitudinal direction of the elongated shaft, wherein the length of the plug is smaller than twice a diameter of the elongated shaft.

I. The system of any one of statements A to H, further comprising an interconnecting cable (42) with optical fibers for interconnecting the illumination fiber (40) and the detection fiber (41) with the optical switch (65).

J. The system of any one of statements A to I, wherein the elongated shaft (10) further comprises a tracking modality for tracking the elongated shaft within a tissue.

K. The system of any one of statements A to J, wherein the elongated shaft comprises at least three channels, with one channel being configured as an injection or extraction channel.

L. The system of any one of statements A to K, further comprising a display device (68).

M. The system of any one of statements A to M, wherein the system is adapted to perform at least one out of the group consisting of diffuse reflectance spectroscopy, diffuse optical tomography, differential path length spectroscopy, and Raman spectroscopy.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements or. steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS

10 shaft
20 core
22 cladding
24 buffer
30 bevel surface
35 injection/retraction channel
40 illumination fiber
41 detection fiber
42 optical cable
45 front surface
50 plug
52 phosphoric element
55 first surface
56 second surface
60 console
64 light source
65 optical switch
66 light detector
68 monitor
70 suction device
80 device for ex-vivo tissue inspection
90 storage container

The invention claimed is:

1. A system for tissue inspection, comprising:
a light source, a spectrometer, an optical switch and a processing unit,
an elongated shaft including a distal end surface,
an illumination fiber having a front surface, wherein the illumination fiber is made of a first optical material having a first refractive index and is arranged in the elongated shaft so that the front surface is located inside the elongated shaft and adjacent to the distal end surface of the elongated shaft, wherein the illumination fiber is configured to receive light from the light source,
a plug of second optical material with a first surface and a second surface, wherein the plug is arranged in front of the illumination fiber so that the first surface of the plug faces the illumination fiber and is optically connected with the illumination fiber, and so that the second surface is located adjacent the distal end surface of the elongated shaft for making contact with a tissue in front of the distal end surface and for emitting illumination light transmitted through the optical plug into said tissue, wherein the second optical material has a second refractive index, and wherein the second refractive index differs from the first refractive index for back reflecting the light from the light source in the illumination fiber via Fresnel reflection, and a detection fiber having a front surface, wherein the detection fiber is arranged in the elongated shaft so that the front surface is located adjacent the distal end surface for making contact with the tissue in front of the distal end surface, wherein the illumination fiber is capable of transmitting light from the light source (64) to its front surface and is capable of transmitting light from the plug to the optical switch (65), and wherein the detection fiber is capable of transmitting light reflected from a portion of the tissue in front of the distal end surface to the optical switch, wherein the optical switch is configured to provide the light from the illumination fiber to the spectrometer for generating a reference spectrum and to provide the light from the detection fiber to the spectrometer for generating a diffuse reflectance spectrum, wherein the processing unit is configured to generate a tissue spectrum by normalizing the diffuse reflectance spectrum with the reference spectrum.

2. The system of claim 1, wherein an element made of a third material is provided between the front surface of the illumination fiber and the plug, wherein the third material comprises phosphor, wherein the illumination fiber is further capable of transmitting phosphorescence light and wherein the optical switch is further capable of providing the phosphorescence light to the spectrometer for generating the reference spectrum.

3. The system of claim 2, wherein the light source comprises an LED or laser light source for exciting the phosphor of the element between the illumination fiber and the plug.

4. The system of claim 1, wherein the light source is adapted to emit light pulses.

5. The system of claim 1, wherein the elongated shaft (10) further comprises a bevel so that the distal end surface is arranged with an acute angle to a longitudinal axis of the elongated shaft.

6. The system of claim 1, wherein a reflective coating is provided at a channel wall of at least one of the channels.

7. The system of claim 1, wherein the at least one of the second surface of the plug and the front surface of the detection fiber has a predetermined roughness.

8. The system of claim 1, wherein the plug has a length in a longitudinal direction of the elongated shaft, wherein the length of the plug is smaller than twice a diameter of the elongated shaft.

9. The system of claim 8, further comprising an interconnecting cable with optical fibers for interconnecting the illumination fiber and the detection fiber with the optical switch.

10. The system of claim 1, wherein the elongated shaft further comprises a tracking modality for tracking the elongated shaft within a tissue.

11. The system of claim 1, wherein the elongated shaft comprises at least three channels, with one channel being configured as an injection or extraction channel.

12. The system of claim 11, further comprising a display device (68).

13. The system of claim 12, wherein the system is adapted to perform at least one out of the group consisting of diffuse reflectance spectroscopy, diffuse optical tomography, differential path length spectroscopy, and Raman spectroscopy.

* * * * *